(12) United States Patent
Doran et al.

(10) Patent No.: US 6,271,378 B1
(45) Date of Patent: Aug. 7, 2001

(54) PROCESS FOR PREPARING TRICYCLIC COMPOUNDS HAVING ANTIHISTAMINIC ACTIVITY

(75) Inventors: Henry J. Doran, Bray Co. Wicklow; Pat M. O'Neill, Arklow, both of (IE)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/464,572

(22) Filed: Dec. 16, 1999

Related U.S. Application Data

(60) Provisional application No. 60/112,922, filed on Dec. 18, 1998.

(51) Int. Cl.$^7$ ................................. C07F 9/28; C07F 9/06; C07D 401/04; C07D 221/06
(52) U.S. Cl. ................................................ 546/21; 546/93
(58) Field of Search ......................................... 546/93, 21

(56) References Cited

U.S. PATENT DOCUMENTS 4,282,233   8/1981   Vilani ................... 424/267

(List continued on next page.)

OTHER PUBLICATIONS

Morrison and Boyd, Organic Chemistry, Editorial Interamericana, Mexico, p. 620 (Spanish Text, English language equivalent of reference herein included).

(List continued on next page.)

*Primary Examiner*—Evelyn Mei Huang
(74) *Attorney, Agent, or Firm*—Arthur Mann; William Lee

(57) ABSTRACT

Disclosed is a process for preparing a compound having the formula:

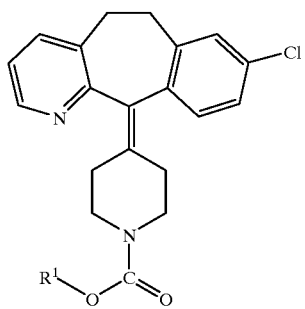

(I)

wherein $R^1$ is selected from the group consisting of: alkyl, alkenyl, alkynyl, aryl, aralkyl, cycloalkyl, and cycloalkylalkyl, $R^1$ being optionally substituted by substituents selected from halo, —OH, alkyl, alkoxy, or —CF$_3$, said process comprising the following steps:

(a) reacting a ketone having the formula

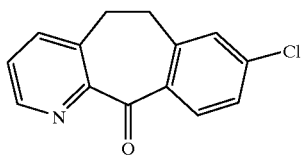

with a carbanion having the formula

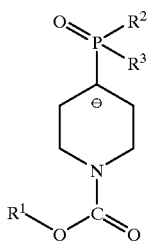

wherein $R^1$ is as defined above, and $R^2$ and $R^3$ are independently selected from the group consisting of —OR$^A$ and —R$^A$, wherein $R^A$ is alkyl, phenyl, substituted phenyl, cycloalkyl, substituted cycloalkyl, cycloalkylalkyl, or substituted cycloalkylalkyl;

(b) treating the reaction mixture from step (a) with a protonating agent; and (c) thermally decomposing the product of 16, to form the compound of formula (I). The compounds made by this process have antihistaminic activity, e.g., loratadine. Also disclosed are novel intermediates having the formula

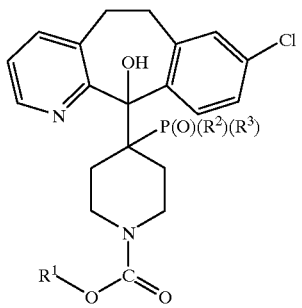 and 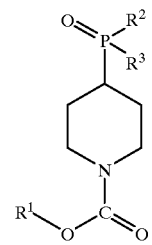

wherein $R^1$, $R^2$ and $R^3$ are as defined above.

16 Claims, No Drawings

U.S. PATENT DOCUMENTS

| | | | |
|---|---|---|---|
| 4,355,036 | 10/1982 | Vilani | 424/267 |
| 4,659,716 | 4/1987 | Villani et al. | 514/290 |
| 5,714,609 | 2/1998 | Doll et al. | 546/93 |
| 5,721,236 | 2/1998 | Bishop et al. | 514/255 |
| 5,852,034 | 12/1998 | Njoroge et al. | 514/290 |
| 5,861,395 | 1/1999 | Taveras et al. | 514/232.8 |
| 5,874,442 | 2/1999 | Doll et al. | 514/290 |
| 5,877,177 | 3/1999 | Taveras | 514/254 |
| 5,925,639 | 7/1999 | Doll et al. | 514/254 |
| 5,925,648 | 7/1999 | Cooper et al. | 514/290 |
| 5,925,757 | 7/1999 | Mallams | 544/361 |
| 5,939,416 | 8/1999 | Rane et al. | 514/228.8 |

OTHER PUBLICATIONS

Becker, et al., Organikum 16 Auflage. Ve. Berlin 1986, p. 189 (German Text, English language equivalent of reference herein included).

Akiba et al., "Regiospecific Introduction of Alkyl Groups into 4–Position of Pyridine Novel Synthesis of 4–Substituted Pyridines", Tetrahedron Letters, vol. 22, No. 41, pp. 4093–4096 (1981).

A.W. Johnson, "Ylides and Imines of Phosphorus," Chaps. 10 and 11, pp. 307–383 (John Wiley & Sons 1993).

Kehler et al., "Syntheses of Novel Piperidin–4–ylphosphinic acid, and piperidin–4–ylphosphonic acid analogues of the inhibitory neurotransmitter 4–aminobutyric acid (GABA)," *J. Chem. Soc., Perkin Trans.* 1, pp. 3241–3243 (1998).

*Chemical Abstracts,* vol. 89, No. 5, Abstract No. 43616, XP–002136558, B.D. Abiyurov et al., "Saturated und unsaturated heterocyclic organophosphorus compounds," *Tr. Inst. Khim. Nauk. Akad. Nauk Kaz.* SSR, No. 46, pp. 139–146 (1978).

C.H. Chen et al., "Synthesis and Reactions of (4H–and 2H–2,6–Diphenylthiopyran–4–yl) phosphonates," *J. Org. Chem.,* vol. 45, No. 12, pp. 2453–2458 (1980).

A.R. Katrizky et al., "Synthetic Applications of N,N Linked Heterocycles. Part 11. Regiospecific Synthesis of Dialkyl Pyridin–4–yl, Quinolin–4–yl, and Isoquinolin–1–yl–phosphonates," *J. Chem. Soc. Perkin Trans.* 1, No. 3, pp. 658–671 (1981).

PROCESS FOR PREPARING TRICYCLIC COMPOUNDS HAVING ANTIHISTAMINIC ACTIVITY

This application claims the benefit of U.S. Provisional Application No. 60/112,922, filed Dec. 18, 1998.

BACKGROUND OF THE INVENTION

This invention provides an improved process and novel intermediates for preparing antihistamines. In particular, the process and the intermediates of this invention are useful in the preparation of loratadine, disclosed in U.S. Pat. No. 4,282,233, and descarboethoxyloratadine (8-chloro-6,11-dihydro-11-(4-piperidylidene)-5H-benzo[5,6]cyclohepta[1,2-b]pyridine) ("DCL"), disclosed in U.S. Pat. No. 4,659,716.

U.S. Pat. No. 4,659,716 discloses the following process for preparing loratadine and DCL:

Braun reaction with ethyl chloroformate to produce loratadine. DCL may be prepared by decarbalkoxylating loratadine. This process suffers from a number of serious drawbacks. The halide, 4-chloro-N-methylpiperidine, required for the Grignard reaction with the ketone (1) is accessible only by a 5 step synthesis, and is unstable at temperatures above ambient temperature. The reaction of ketone (1) with N-methylpiperidin-4-yl magnesium chloride to produce the alcohol (2) is not a high yielding reaction (about 60%) due to the ocurrence of conjugate addition (i.e., to the pyridine ring) and reduction. The dehydration of alcohol (2) to produce compound (3) is a sensitive reaction, and isomerization of compound (3) can occur. The Von Braun reaction of compound (3) to produce loratadine produces noxious chloromethane as a gaseous by-product. This noxious by-product must be decomposed chemically before discharge to the atmosphere. These problems are eliminated by the present invention.

SUMMARY OF THE INVENTION

This invention provides a process for preparing a compound having the formula:

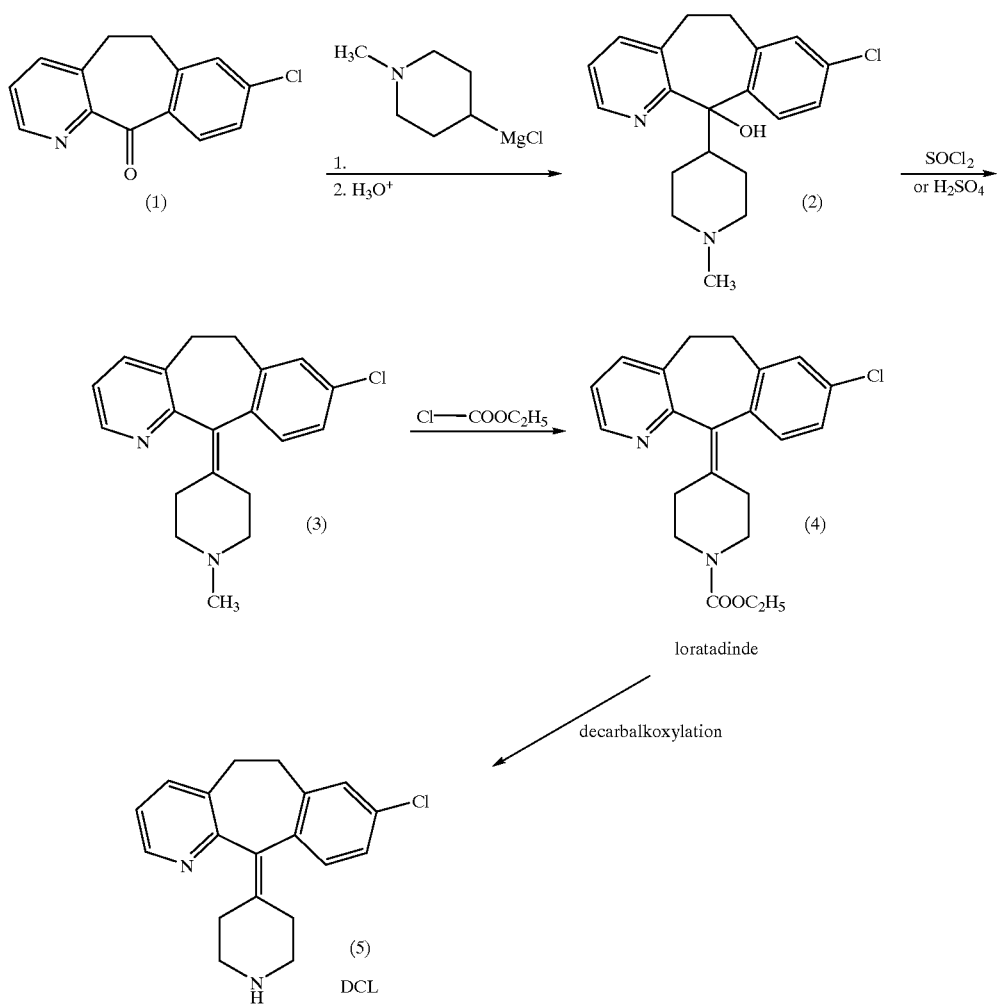

According to this process, the tricyclic ketone (1) is coupled with Grignard reagent derived from 4-chloro-N-methylpiperidine. The alcohol (2) derived from this addition reaction is dehydrated under acidic conditions to produce compound (3). Compound (3) is then subjected to a Von (I)

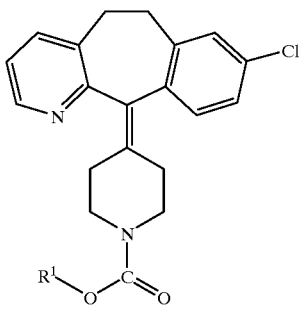

wherein R¹ is selected from the group consisting of: alkyl, alkenyl, alkynyl, aryl, aralkyl, cycloalkyl, and cycloalkylalkyl, R¹ being optionally substituted by substituents selected from halo, —OH, alkyl, alkoxy, or —CF₃, said process comprising the following steps:

(a) reacting a ketone having the formula

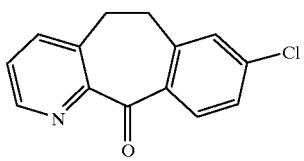

with a carbanion having the formula

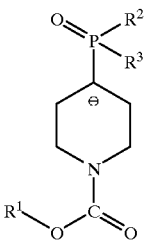

wherein R¹ is as defined above, and R² and R³ are independently selected from the group consisting of —OR$^A$ and —R$^A$, wherein R$^A$ is alkyl, phenyl, substituted phenyl, cycloalkyl, substituted cycloalkyl, cycloalkylalkyl, or substituted cycloalkylalkyl;

(b) treating the reaction mixture from step (a) with a protonating agent to form a β-hydroxy intermediate having the formula

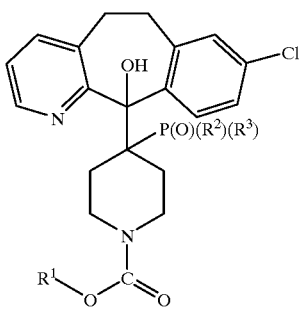

wherein R¹, R² and R³ are as defined above; and (c) thermally decomposing the β-hydroxy intermediate to form the compound of formula (I).

This invention further provides a process for preparing a compound having the formula:

(IV)

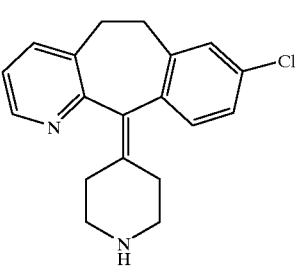

said process comprising the following steps:

(a) reacting a ketone having the formula

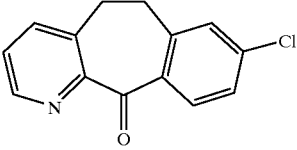

with a carbanion having the formula

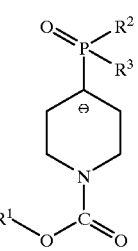

wherein R¹ is selected from the group consisting of: alkyl, alkenyl, alkynyl, aryl, aralkyl, cycloalkyl, and cycloalkylalkyl, R¹ being optionally substituted by substituents selected from halo, —OH, alkyl, alkoxy, or —CF₃; and R² and R³ are independently selected from the group consisting of —OR$^A$ and —R$^A$, wherein R$^A$ is alkyl, phenyl, substituted phenyl, cycloalkyl, substituted cycloalkyl, cycloalkylalkyl, or substituted cycloalkylalkyl;

(b) treating the reaction mixture from step (a) with a protonating agent to form a β-hydroxy intermediate having the formula

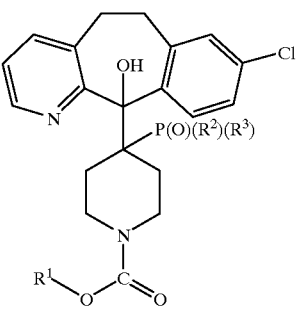

wherein R¹, R² and R³ are as defined above;

(c) thermally decomposing the β-hydroxy intermediate to form a compound having the formula

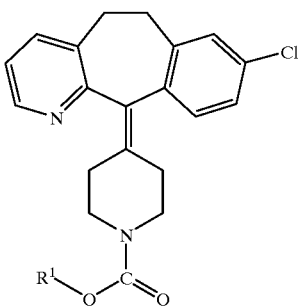

(I)

wherein R¹ is as defined above; and (d) converting the compound of formula (I) to the compound of formula (IV).

In a particularly preferred embodiment for preparing compound (IV) (DCL), R¹ in the foregoing process is selected for ease of removal under acidic conditions, and is preferably alkyl, most preferably t-butyl.

This invention firer provides a novel intermediate having the formula

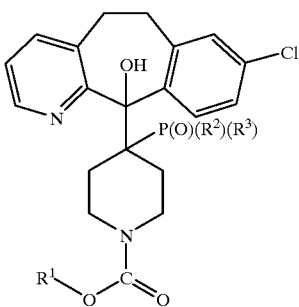

II wherein R¹, R², and R³ are as defined above.

Also provided is a novel intermediate having the formula

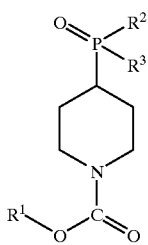

(III)

wherein R¹, R², and R³ are as defined above.

DETAILED DESCRIPTION

As used herein, the term "alkyl" means straight or branched hydrocarbon chains of 1 to 6 carbon atoms.

"Alkenyl" refers to straight or branched hydrocarbon chains of 1 to 6 carbon atoms having at least one carbon to carbon double bond.

"Alkynyl" refers to straight or branched hydrocarbon chains of 1 to 6 carbon atoms having at least one carbon to carbon triple bond.

"Aryl" refers to a carbocyclic group having at least one aromatic ring (e.g., phenyl or naphthyl).

"Aralkyl" refers to a group having the formula aryl-R—, wherein R is alkyl.

"Cycloalkyl" refers to a non-aromatic carbocyclic ring of from 3 to 6 carbon atoms.

"Cycloalkylalkyl" refers to a group having the formula cycloalkyl-R—, wherein R is alkyl.

"Halo" refers to fluorine, chlorine, bromine or iodine radicals.

"Substituted phenyl" refers to phenyl substituted by substituents selected from halo, —OH, alkyl, alkoxy, or —CF₃.

"Substituted cycloalkyl" refers to cycloalkyl substituted by substituents selected from halo, —OH, alkyl, alkoxy, or —CF₃.

"Substituted cycloalkylalkyl" refers to cycloalkylalkyl, wherein the cyloalkyl portion is substituted by substituents selected from halo, —OH, alkyl, alkoxy, or —CF₃.

The present process is a significant improvement over prior art processes for preparing loratadine and related compounds. One significant advantage is that the starting ketone can be converted to the desired product (e.g., loratadine) as a one pot process (i.e., without isolating the β-hydroxy intermediate) with high yield and purity. The carbanion used in the present process is derived from the thermally stable compound of formula (III), which is considerably more stable than the thermally labile 4-chloro-N-methyl piperidine disclosed in U.S. Pat. No. 4,659,716. Moreover, the compound of formula (III) can be obtained from pyridine in two steps, in about 70% yield, which is a much simpler preparation than the five steps required to prepare the 4-chloro-N-methyl piperidine used in the prior art process.

R¹ is preferably alkyl, more preferably ethyl or t-butyl, most preferably, ethyl.

R² and R³ are preferably alkyl, more preferably, methyl, ethyl, isopropyl, or t-butyl, and most preferably ethyl.

When R¹, R², and R³ are substituted, the number of substituents is preferably 1 to 3.

The carbanion used in step (a) of our process is preferably generated by treating the compound of formula (III), above, with a strong base in a suitable aprotic organic solvent. Preferably, the base is an organolithium base. Examples of suitable bases include, but are not limited to lithium diisopropyl amide ("LDA"); n-butyl lithium; t-butyl lithium; sec-butyl lithium; and lithium diethylamide. LDA is most preferred. Examples of suitable aprotic organic solvents for generating the carbanion, and for carrying out step (a), include, but are not limited to: xylene; tetrahydrofuran ("THF"); diethyl ether; ethylene glycol dimethyl ether; tert-butyl methyl ether; diethylene glycol dimethyl ether; benzene; toluene, and mixtures thereof. Preferably, the solvent employed in step (a) is an ether, most preferably, THF. In a particularly preferred embodiment, step (a) is carried out in a mixture of an ether solvent with a non-ether solvent having a higher boiling point. Step (a) is preferably carried out at a temperature of −150° to +10° C., more preferably, −80° to −10° C., most preferably, −40° to −20° C. Preferably, the compound of formula (III), and the carbanion generated therefrom, are used in amounts ranging from 1 to 3 equivalents, more preferably, 1 to 1.5 equivalents, most preferably, 1.05 to 1.1 equivalents relative to the ketone.

Step (b) of our process is carried out by adding a protonating agent to the reaction mixture from step (a). Without being bound by theory, it is believed that the carbanion and the tricyclic ketone react in step (a) to form the following alkoxide intermediate, which is unstable:

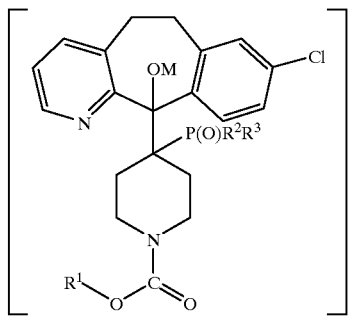

M = alkali metal atom, e.g., lithium

The protonating agent is added to convert this unstable alkoxide to the β-hydroxy intermediate. Preferably, the protonating agent is used in amounts ranging from 1 to 3 equivalents, more preferably, 1 to 1.5 equivalents, most preferably, 1.05 to 1.1 equivalents relative to the ketone. The protonating agent is preferably water or an acid. When the protonating agent is an acid, the present process may be carried out without isolating the β-hydroxy intermediate. Suitable acids for use as the protonating agent include, but are not limited to, mineral acids in alcohol (e.g., methanolic anhydrous sulfuric acid and methanolic hydrochloric acid), sulfonic acids, and $C_1$ to $C_6$ alkanoic acids. Preferably, the acid is anhydrous. Acetic acid is particularly preferred. Once the reaction is quenched with acid, preferably anhydrous acid, the solvent from step (a) (preferably a low-boiling ether solvent) may be removed by adding a higher boiling solvent and heating the mixture to a temperature above the boiling point of the lower boiling solvent. The thermal decomposition step (c) can be carried out by refluxing this mixture, preferably at a temperature of from 110° to 160° C., more preferably, 110° to 140° C., most preferably 130° to 140° C., to produce compound (I). The higher boiling solvent preferably has a boiling point of from 110° to 160° C., more preferably, 110° to 140° C., most preferably 130° to 140° C. Suitable higher boiling solvents include, but are not limited to xylene, chlorobenzene, alkanes, and alcohols. Compound (I) is preferably recovered by distilling off the higher boiling solvent, dissolving the residue in acetonitrile, distilling down to dryness, and recrystallizing from acetonitrile. This recrystallization effectively removes the only observed contaminants, which are small amounts of the starting tricyclic ketone and the phosphonate or phosphine oxide used to generate the carbanion.

If water is used as the protonating agent, it is preferable to isolate the β-hydroxy intermediate, which is very soluble in water. Thus, when water is added to the reaction mixture from step (a), the resulting organic and aqueous phases may be separated, and the β-hydroxy intermediate may be recovered from the aqueous phase. The recovery is preferably carried out by treating the aqueous solution with an inorganic salt (e.g., potassium carbonate) in the presence of an organic solvent in which the β-hydroxy intermediate is soluble (e.g., THF). The β-hydroxy intermediate may be purified by recrystallization. Step (c) can then be carried out by refluxing a suspension of the purified β-hydroxy intermediate in a high boiling solvent. Compound (I) can then be recovered by removing the solvent by distillation, and recrystallizing from a suitable solvent (e.g., acetonitrile).

When DCL is the desired product, it may be prepared by carrying out the foregoing process to obtain a compound of formula (I), and converting the compound of formula (I) to DCL by conventional means. For example, the compound of formula (I) can be coverted to DCL by treating it with a strong base, e.g., KOH or NaOH, or with an acid, e.g., trifluoroacetic acid, aqueous sulfuric acid, or para-toluene sulfonic acid. When DCL is the desired product, $R^1$ is preferably selected for ease of removal under acidic conditions, and is preferably alkyl, most preferably t-butyl.

The compound of formula (III) is prepared as shown in the following scheme:

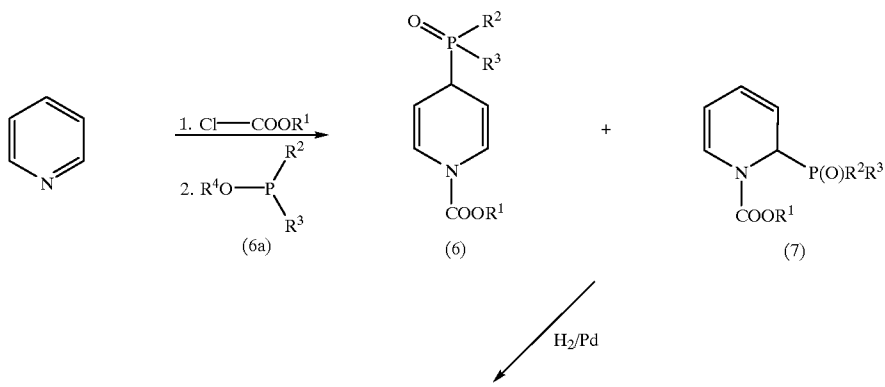

-continued

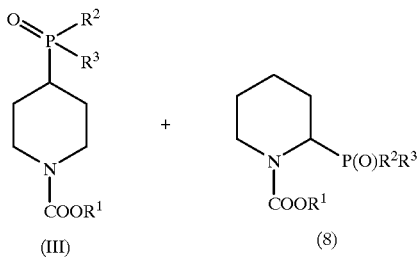

As shown above, pyridine is sequentially treated with a chloroformate, Cl—COOR$^1$, where R$^1$ is as defined above, in a suitable solvent (preferably acetonitrile), followed by treatment with compound 6a, wherein R$^2$ and R$^3$ are as defined above, and R$^4$ is alkyl, preferably methyl or ethyl, with ethyl being particularly preferred. The sequential treatment yields compound 6, and a small amount of compound 7. The mixture of compounds 6 and 7 is then subjected to catalytic hydrogenation, using a suitable metal catalyst, preferably palladium, to produce the desired compound of formula (III) and small amounts of compound 8, a 1,2-isomer of the compound of formula (III). Preferably, the product obtained from the catalytic hydrogenation is treated with 15% aqueous HCl which selectively destroys the 1,2-isomer, resulting in higher purity of the compound of formula (III). Compound (III) can be further purified by distillation to remove compound 8, which has a lower boiling point. If the desired compound of formula (III) has an R$^1$ group that is sensitive to catalytic hydrogenation, such a compound can be prepared from a compound of formula (III) wherein R$^1$ is ethyl, by decarboethoxylation with either acid or base, and reacting the resulting compound with a chloroformate, Cl—COOR$^1$, having the desired R$^1$ group.

Compounds within the scope of compound 6a are either commercially available, or are known compounds that can be prepared by known methods. If the substituents of compound 6a are not all the same, such a compound may be prepared by reacting one mole of PCl$_3$ or PBr$_3$ with one mole of ethanol or methanol to displace one halogen group with methoxy or ethoxy, and then sequentially reacting the resulting compound with one mole of alcohol or Grignard reagent to sequentially displace the two remaining halogen groups with the desired R$^2$ and R$^3$ groups. The tricyclic ketone used in our process may be prepared according to methods known in the art, e.g., by the methods disclosed in U.S. Pat. Nos. 4,659,716, 4,731,447, or PCT Publication WO96/31478, published Oct. 10, 1996. Alternatively, the tricyclic ketone may be prepared according to the following scheme:

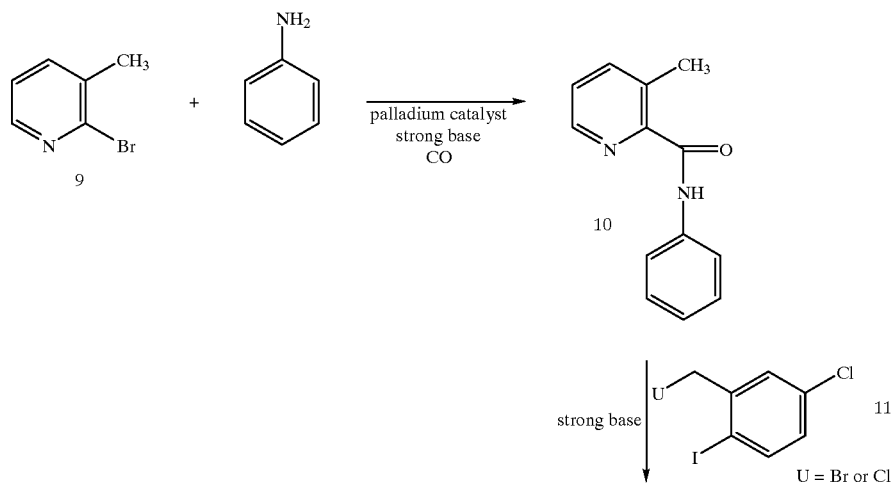

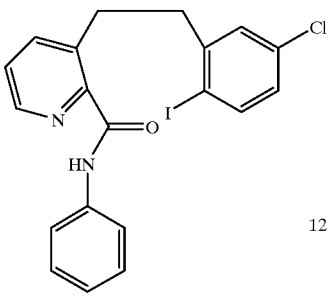

12

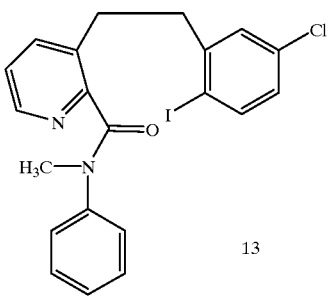

13

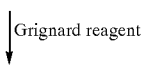

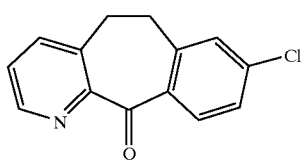

As shown in the scheme above, the pyridine compound 9 is reacted with aniline in the presence of a palladium catalyst, e.g., Pd(OAc)$_2$ or PdCl$_2$, carbon monoxide, a base, e.g., 1,8-diazabicyclo-[5.4.0]undec-7-ene ("DBU") or diisopropylethylamine, and an ether selected from ethylene glycol dimethyl ether, 2-methoxyethyl ether, and triethylene glycol dimethyl ether, to form amide compound 10. The reaction to form amide compound 10 is preferably carried out at a temperature of about 45° C. to 90° C., and a pressure of about 40 to 100 psi, in a suitable solvent, e.g., toluene or chlorobenzene. Amide compound 10 is reacted with an iodo-substituted compound 11 in the presence of a strong base, e.g., lithium diisopropylamide, in a suitable solvent, e.g., THF, to form compound 12. Compound 12 is reacted with CH$_3$I and a base, e.g., NaH to form methylated compound 13. Compound 13 is cyclized to form the desired ketone by reaction with a Grignard reagent, e.g., 2-methoxyphenylmagnesium bromide.

Alternatively, the tricyclic ketone may be prepared according to the following scheme:

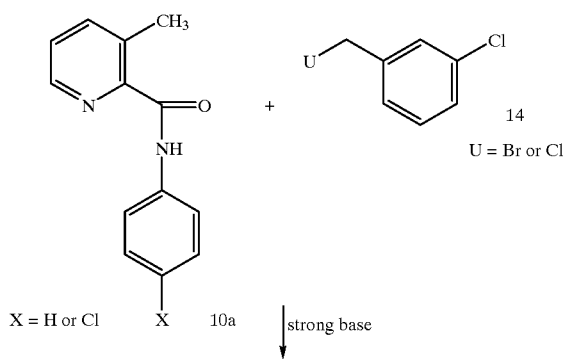

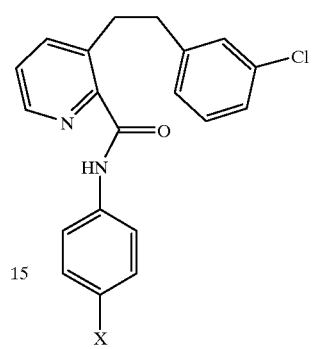

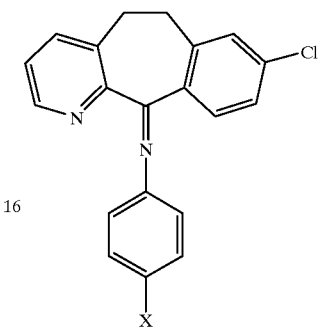

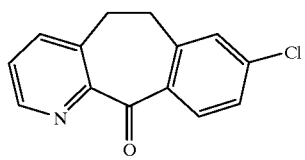

As shown in the scheme above, amide compound 10a is reacted with compound 14 in the presence of a strong base, e.g., lithium diisopropylamide, in a suitable solvent, e.g., THF to form compound 15. Compound 15 is cyclized by treating it with a dehydrating agent and a super acid, e.g., P$_2$O$_5$/CF$_3$SO$_3$H or a dehydrating agent and a Lewis acid, e.g., PCl$_5$/AlCl$_3$ or POCl$_3$/ZnCl$_2$, and hydrolyzing the reaction product 16 to form the desired tricyclic ketone.

The amide compound 10a can be prepared as shown below:

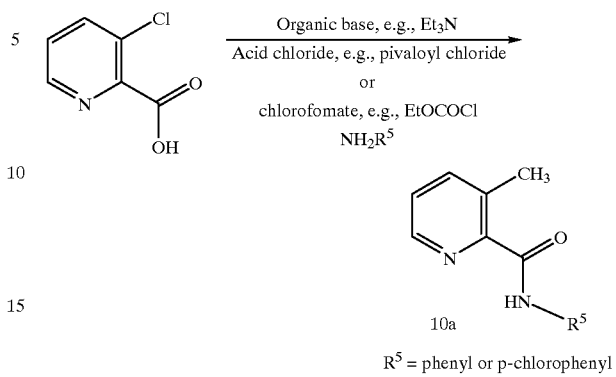

R$^5$ = phenyl or p-chlorophenyl

As shown above, 3-methylpicolinic acid is reacted with an organic base, e.g., triethylamine, followed by an acid chloride, e.g., pivaloyl chloride or a chloroformate, e.g., C$_2$H$_3$OCOCl, in a suitable solvent such as dichloromethane at a temperature of about −30° C. to 0° C. to give a mixed anhydride. To the mixture is added NH$_2$R$^5$ at a temperature of −30° C. to 0° C. either neat or as a solution in a suitable solvent to form amide compound 10a.

The following examples illustrate the foregoing invention, although such examples should not be construed as limiting the scope of the invention. Alternative reagents and analagous processes within the scope of the invention will be apparent to those skilled in the art.

PREPARATION A

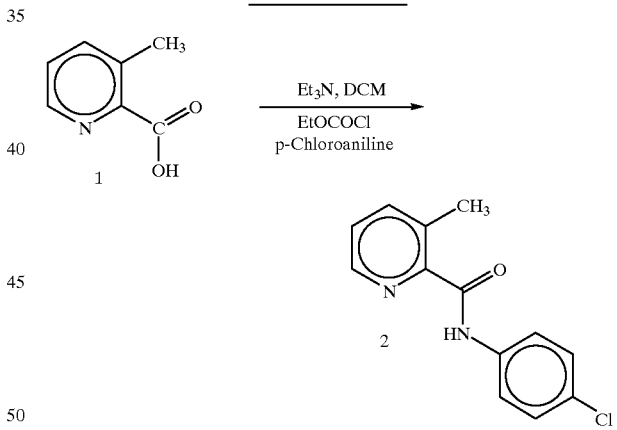

To a suspension of 3-methyl-picolinic acid (400 g; 2.92 mol) in dichloromethane ("DCM") (1600 ml) is added triethylamine (406.4 ml; 2.92 mol). The solution is cooled to −20° C. and ethylchloroformate (278.8 ml; 2.92 mol) is added dropwise while maintaining the reaction temperature between −10 and −20° C. The reaction mixture is stirred at this temperature for a further two hours. A solution of 4-chloroaniline (372.1 g; 2.92 mol) in dichloromethane (150 ml) is then added dropwise again while maintaining an internal temperature of between −10 and −20° C. Stirring at this temperature is continued for two hours, and then the reaction is allowed to warm to room temperature. The reaction is quenched by the addition of water (400 ml). The phases are separated and the organic layer is washed with water (400 ml). The reaction mixture is concentrated to about 800 ml by removing the solvent under vacuum. Isopropanol (400 ml) is added and one volume of solvent is removed under reduced pressure. Isopropanol (400 ml) is added and the solvent is again removed under reduced pressure, concentrating to 800 ml. Isopropanol (1200 ml) is added and the mixture heated to between 70 and 80° C. The mixture is cooled to 60° C. and seeded. The mixture is held at this temperature for 30 minutes, then cooled to between 0 and −5° C., and held at this temperature for one hour. The product is removed by filtration, washing on the pump with chilled isopropanol. The product is dried at 60° C. in a vacuum oven to give 655.8 g of amide 2 (91%).

PREPARATION B

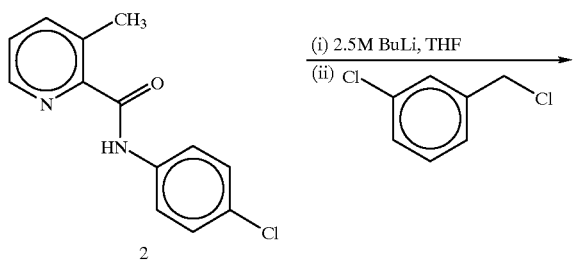

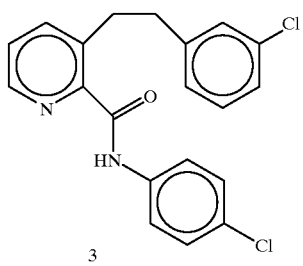

To a solution of amide 2 (150 g; 0.61 mol) in THF (750 ml) at −25° C. was added a solution of 2.5M butyllithium in hexane (486 ml; 1.22 mol), while maintaining an internal temperature of between −20 and −30° C. The mixture was stirred for one hour at −25° C., followed by the dropwise addition of 3-chlorobenzyl chloride over 55 minutes, again maintaining an internal temperature of between −20 and −30° C. The reaction mixture was stirred at −25° C. for one hour, and then allowed to warm to room temperature. Water (300 ml) was added, and the resulting mixture was stirred for 30 minutes. The phases were separated and the aqueous phase was extracted further with ethyl acetate (150 ml). The combined organic phase was evaporated to dryness under vacuum and the residue crystallised from isopropanol (900 ml) to give 205.5 g of amide 3 (91%).

PREPARATION C

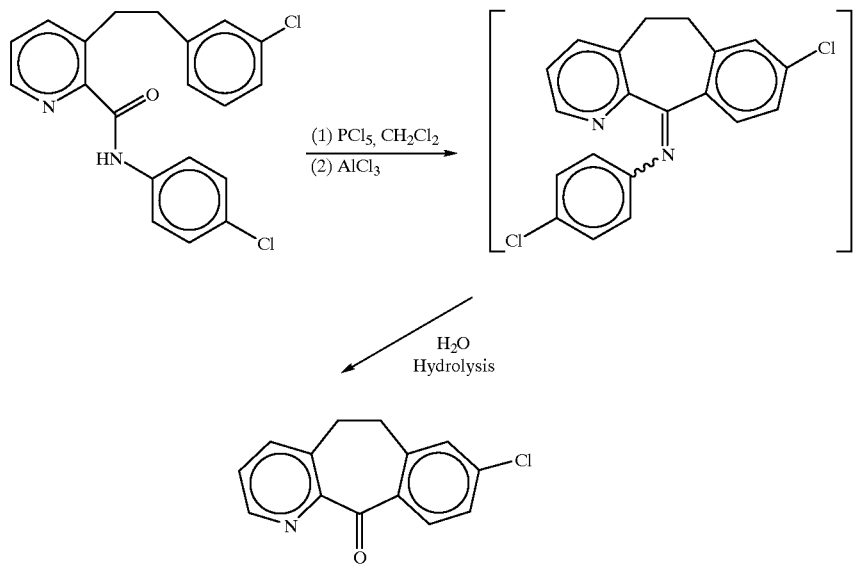

To a solution of phosphorous pentachloride (95%, 26.6 g; 0.121 mol) in dichloromethane (60 ml) at 5° C. was added a solution of N-(4-chlorophenyl)-3-[2-(3-chlorophenyl)ethyl]-2-pyridine carboxamide (30 g; 0.081 mol) in dichloromethane (60 ml) dropwise over 20 minutes. The resuting mixture was stirred at 5 to 10° C. for one hour, then allowed to warm to room temperature over thirty minutes. Aluminum chloride (43.1 g; 0.323 mol) was added in four portions over 45 minutes while maintaining a reaction temperature below 30° C. The mixture was stirred for one hour, then poured onto ice (300 g). The dichloromethane was removed from the mixture by distillation followed by heating the remaining aqueous solution to 80° C. for one hour. Citric acid trisodium salt dihydrate (70 g; 0.24 mol) was added followed by aqueous sodium hydroxide solution (10M, 140 ml) to adjust the pH to 7. Toluene (150 ml) was added, followed by a solution of maleic anhydride (12.0 g 0.122 mol) in toluene (50 ml). The resulting mixture was stirred for 30 minutes and the pH of the aqueous phase adjusted to 12 with aqueous sodium hydroxide solution (10M, 60 ml). The mixture was heated to 70° C. and the phases separated. The aqueous phase was further extracted with toluene (2×90 ml) and the combined organic layers washed with water (90 ml). An HPLC assay indicated a solution yield of ketone product of 95%. The product mixture was recrystallised from toluene/hexane to give the desired tricyclic ketone (13.96 g, 71%) as an off-white solid.

EXAMPLE 1

A. Diethyl N-ethoxycarbonyl-1,4-dihydropyridine-4-phosphonate

A solution of pyridine (16.1 L, 0.2 kmol) in acetonitrile (160 L) is cooled to −10° C. Ethyl chloroformate (19.1 L, 0.2 kmol) is added at such a rate that the temperature does not rise above 0° C. The suspension is then stirred at −10 to 0° C. for 2 hours to ensure complete N-acylation. The batch is cooled to −30° C., and triethyl phosphite (34.3 L, 0.2 kmol) is added at such a rate that the temperature does not rise above −20° C. (ranging from −30 to −20° C.). The solution is stirred in this range for 2 hours, and then warmed to ambient temperature over several hours (or overnight). The acetonitrile is stripped under Sihi vacuum to a temperature not exceeding 80° C. and the residual liquid is cooled to 30° C. Dichloromethane (140 L) is added, followed by a mixture of water (60 L) and concentrated HCl (10 L). The mixture is stirred at ambient temperature for 1 hour, and the lower organic phase is pumped to a separate vessel and washed with water (100 L). After pumping back to the original (water-washed) vessel, it is washed with 1% potassium carbonate solution and finally with water to neutrality. The dichloromethane is then stripped to leave crude (about 92% pure) diethyl N-ethoxycarbonyl-1,4-dihydropyridine-4-phosphonate containing about 5% 1,2-isomer and traces of triethyl phosphate (oxidation of corresponding phosphite). The yield is about 48.4 kg of a light yellow liquid which is stored under nitrogen because it is slightly unstable to air.

B. Diethyl N-ethoxycarbonylpiperidine-4-phosphonate

The above crude phosphonate (24 kg) is dissolved in methanol (64 L) and charged to a hydrogenator. The catalyst (5% Pd/C slurry, 3.46 kg) is then charged in methanol (14 L) and washed in with 7.5 L solvent. The mixture is hydrogenated at 10 bar/25° C. until uptake is complete (about 10 hours), after which the hydrogen is vented and purged with nitrogen. The catalyst is filtered and the catalyst washed with methanol (25 L). The methanol is then stripped to leave a quantitative yield of diethyl N-ethoxycarbonylpiperidine-4-phosphonate (5a) containing about 5% of the 1,2-isomer. The material is purified by high vacuum distillation, b.p. 185–90° C./1.5 mbar. The 1,2-isomer is concentrated in the distillation pre-run.

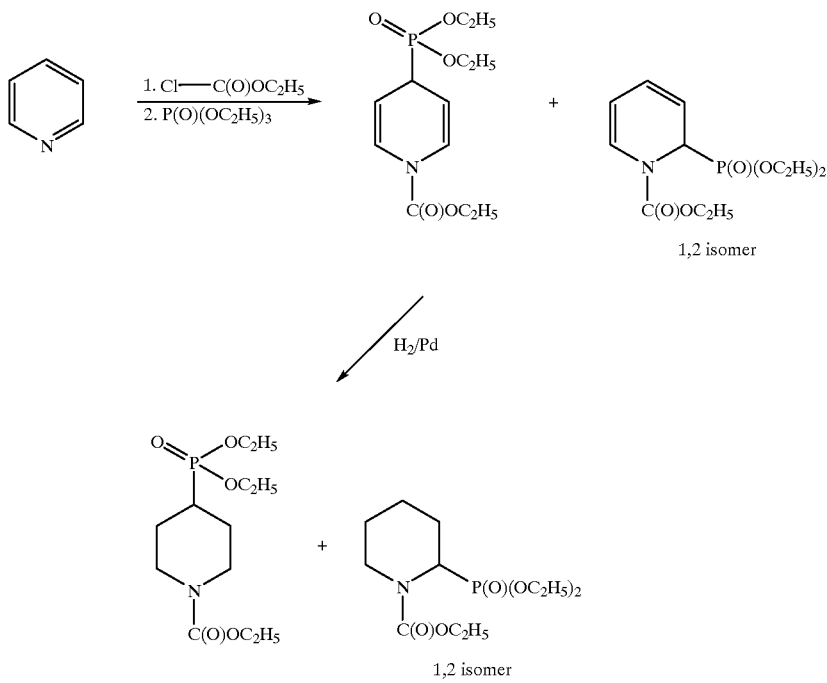

EXAMPLE 2

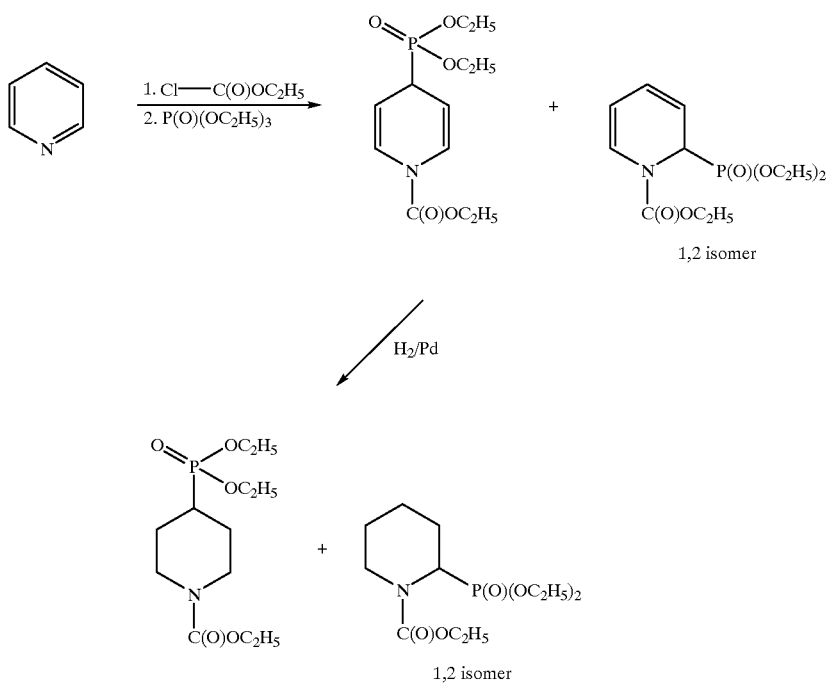

A. Diethyl N-ethoxycarbonyl-1,4-dihydropyridine-4-phosphonate

A solution of pyridine (320 g, 4.05 mol) in acetonitrile (1600 mL) was cooled to −25° C. and treated with ethyl chloroformate (440 g, 4.05 mol) over about 0.75 hours, keeping the temperature below −15° C. A very thick slurry of the intermediate N-ethoxycarbonylpyridinium chloride salt was formed. This suspension was stirred at −30 to −15° C. for 2 hours. Triethyl phosphite (671.2 g, 4.04 mol) was then added over about 1 hour while keeping the temperature in the same range. A yellow solution results. This was allowed to warm to ambient temperature overnight and the solvent was distilled off under vacuum to a maximum temperature of 60° C. The residual oil was dissolved in dichloromethane (2000 mL) and stirred with a mixture of water (500 mL) and concentrated hydrochloric acid (20 mL) at ambient temperature for 3 hours. The phases were separated and the dichloromethane solution washed with water (500 mL) and then with a solution of 1 g potash in 500 mL water. The pH of this wash is checked after IS minutes agitation and if in the 6–8 range, the dichloromethane solution is water-washed again and the solvent is removed under vacuum to a temperature of 70° C. (oil-pump vacuum was used towards the end of the distillation) to leave 1144 g (98%) of diethyl N-ethoxycarbonyl-1,4-dihydropyridine-4-phosphonate (DHP-Phosphonate). This material was a 91:9 mixture of DHP-Phosphonate and its 1,2-isomer.

B. Hydrogenation of DHP-Phosphonate to Diethyl N-ethoxycarbonylpiperidine

The above DHP-Phosphonate (300 g, 1.038 mol) was hydrogenated in methanol at 40° C./10 bar, using 20 g of 50% water-wet Pd/C, until hydrogen uptake ceased (about 5–6 hours). The mixture was then stirred under hydrogen pressure overnight. After a normal workup, 303.8 g (99.9%) of crude diethyl N-ethoxycarbonylpiperidine-4-phosphonate was obtained. This was dissolved in water (305 mL) and concentrated hydrochloric acid (36% aqueous HCl) (208 mL) was added. The solution was stirred at 50–60° C. for 3 hours, cooled to ambient temperature and extracted twice with 300 mL of dichloromethane. The combined organic layers were water-washed, then dilute potash washed and finally water-washed to pH neutrality. The solvent was stripped and the product distilled under high vacuum (1–2 mbar) without the need for fractionation to give 262.9 g of 99.9% pure N-ethoxycarbonylpiperidine-4-phosphonate (81% yield from pyridine).

EXAMPLE 3

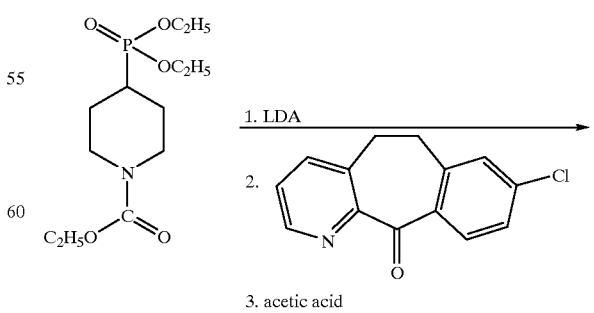

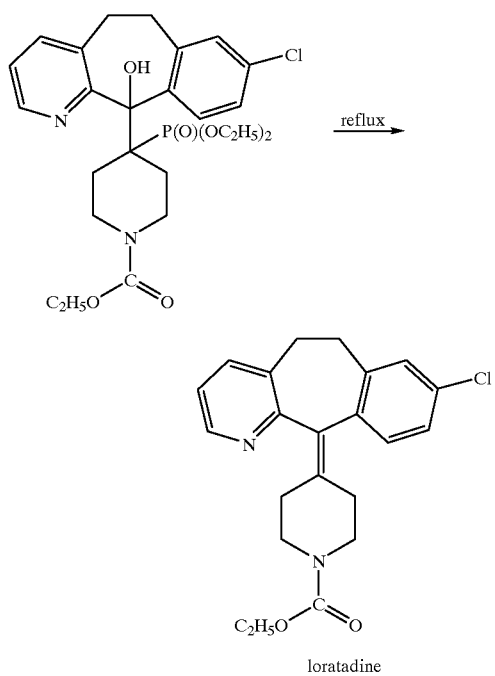

loratadine

Loratadine: Without Isolation of β-hydroxyphosphonate Intermediate

A solution of n-butyllithium in hexane (318 mL of 1.6M, 0.509 mol) is added to a solution of diisopropylamine (53.1 g, 0.526 mol) in xylene: THF (265:525 mL) at −70° C. The resulting solution is stirred at −70 to −60° C. for 1 hour prior to the addition of a solution of diethyl N-ethoxycarbonylpiperidine-4-phosphonate (150 g, 0.489 mol) of 96% pure; rest 1,2-isomer) in xylene (150 mL), prepared according to the method of Example 1. This suspension was stirred at −70 to −60° C. for 0.5 hours and allowed to warm to −20° C. over the course of approximately 1 hour. A solution of the 8-chloro-ketone shown above (111.3 g, 0.457 mol) in xylene: THF (120 mL:240 mL) is added over about 0.5 hours, while keeping the temperature less than −10° C. A dark green solution results. This is stirred in the range of −20 to −10° C. for 1 hour. It is quenched by the addition of acetic acid (36 g, 0.6 mol). TLC analysis [dichloromethane: toluene: methanol:33% aqueous ammonia 100:40:20:1] at this point shows the hydroxyphosphonate, as well as small amounts of unreacted ketone. (Rf about 0.2).

More xylene (450 mL) is added and solvent is distilled off until the solution temperature reaches 135 to 140° C. It is then refluxed for 1 hour, and samples are analysed by TLC until no hydroxyphosphonate is left. The solution is cooled to 60° C. and water (500 mL) is added. The phases are split and the organic solution is washed with 5% formic acid (2×200 mL) and water until neutral. The solution yield of loratadine (by capillary GC-HP-5 column, 80° C./3 min. to 265° C.) is about 90% (about 3 to 5% ketone is left, as well as trace amounts of the alcohol corresponding to the ketone, and some phosphonate is also detected). The xylene is distilled off and the residue is dissolved in acetonitrile (500 mL) and distilled down to dryness. This is repeated once to remove any xylene, since xylene solubilises loratadine. The crude product (204.6 g) is finally recrystallised from acetonitrile (460 mL) and dried at 60° C. in vacuo. The yield of pure loratadine is 130.3 g (74.5%) (pure by TLC and 99.99% pure by capillary GC). A further crop of pure loratadine 3.6 g, 2.0%), can be obtained from the mother-liquor by concentration and cooling. The total yield is 133.9 g (76.5%).

EXAMPLE 4

Loratadine: Isolation of the β-hydroxyphosphonate Intermediate

The reaction is carried out exactly as described in Example 3, above on a scale of 150 g (0.619 mol) of the tricyclic 8-chloro ketone. Instead of an acetic acid quench, the reaction is treated with water (800 mL). The phases are separated and the water phase is heated under vacuum to about 45° C. to remove THF. The solution of the β-hydroxyphosphonate is washed with toluene (2×200 mL). THF (1 L) was then added, followed by potassium carbonate (200 g). The product-containing THF layer was separated and the solvent distilled off under reduced pressure to yield 330 g of a gummy solid which was dissolved in methanol (700 mL). This solution was stirred overnight and cooled to about −30° C. Filtration gave 187.7g (56%) of white β-hydroxyphosphonate. More material (about 50 g, 15%) can be obtained from the methanol mother-liquor if required. The total isolated yield is about 70%. This material contains about 4–7% water which is tenaciously retained.

Pyrolysis of β-hydroxyphosphonate

A suspension of the β-hydroxyphosphonate, isolated according to the procedure above (79 g, 0.147 mol) in xylene (320 mL), was refluxed under a Dean-Stark apparatus and 3 mL water was collected. The mixture was further refluxed for 2 hours to effect complete thermal decomposition. The solution was cooled to 60° C., treated with 200 mL water and the phases separated (the pH of the water phase was about 5). The organic phase was washed several times with warm water and the xylene removed under reduced pressure. The residual material was dissolved in acetonitrile (200 mL) and stripped down to dryness. This was repeated and the residual oil was finally recrystallised from acetonitrile (270 ml) and dried at 60° C. in vacuo. The yield of pure loratadine was 43.44 g (80% ex anhydrous β-hydroxyphosphonate). A second crop (3.5 g, 6.4%) was obtained from the mother-liquor on concentration and cooling.

EXAMPLE 5

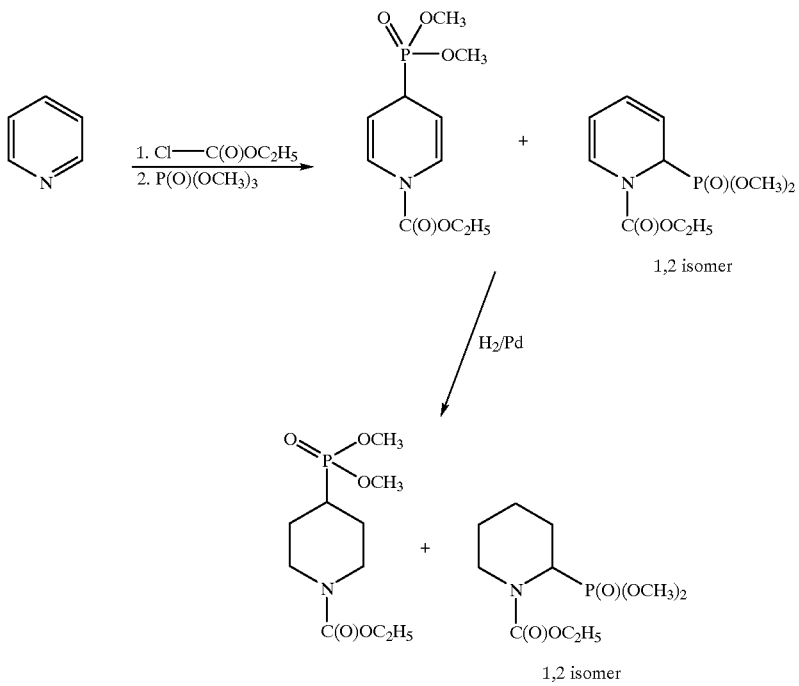

A. Preparation of dimethyl N-ethoxycarbonyl-1,4-dihydropyridine -4-phosphonate

A solution of pyridine (316 g, 4.0 mol) in acetonitrile (4.0 L) was cooled to 0° C. and ethyl chloroformate (434 g, 4.0 mol) was added over about 1.25 hours while keeping the temperature less than 5° C. The resulting yellow suspension was stirred at −5° C. to 0° C. for 1.5 hours. It was then cooled to −25° C. and trimethyl phosphite (496.3 g, 4.0 mol) was added over 1 hour, keeping the temperature less than −20° C. It was allowed to warm to ambient temperature overnight. The solvent was removed under reduced pressure at t<70° C. and the resulting oil was dissolved in dichloromethane (2.8 L) and washed with water (2 L) 5% HCl (2 L), 2% $K_2CO_3$ solution (1 L), and finally water (2 L) to pH neutrality. The solution was then concentrated under reduced pressure to a yellow oil (645 g, 62%) which by capillary GC was a 1:1 mixture of dimethyl N-ethoxycarbonyl-1,4-dihydropyridine-4-phosphonate and dimethyl N-ethoxycarbonyl-1,2-dihydropyridine-2-phosphonate. This material was used directly for the hydrogenation below, since attempted distillation leads to decomposition.

B. Hydrogenation to dimethyl N-ethoxycarbonylpiperidine-4-phosphonate

The above material was hydrogenated in methanol (1600 mL) using 5% Pd/C (80 g of 50% water-wet) at ambient temperature and 15 bar $H_2$. After hydrogenation was complete) the solution was stirred under 15 bar $H_2$ for 20 hours. After venting and purging of the hydrogen, the catalyst was filtered and the solvent concentrated under reduced pressure to give a 1:1 mixture of dimethyl N-ethoxycarbonylpiperidine-4-phosphonate and dimethyl N-ethoxycarbonylpiperidine-2-phosphonate in quantitative yield. This mixture was separated by fractional distillation—the 1,4-isomer being concentrated in the later fractions (b.p. 130–40° C./1 mbar). In this way, 130 g of 98% pure dimethyl N-ethoxycarbonylpiperidine-4-phosphonate was obtained.

EXAMPLE 6

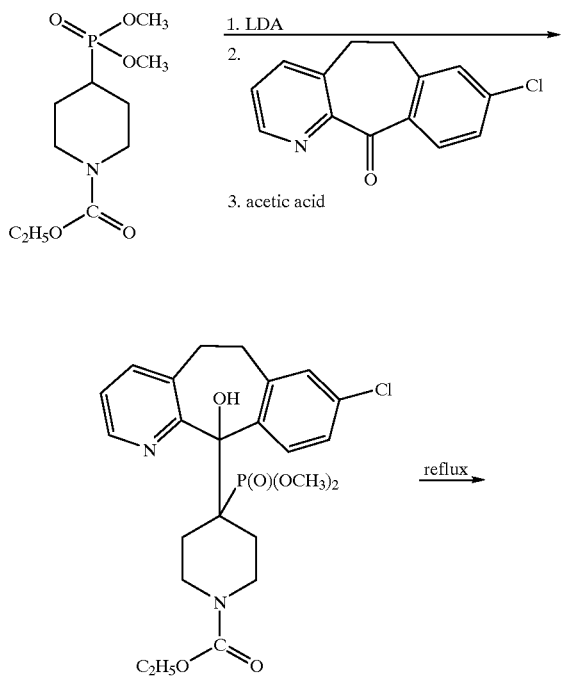

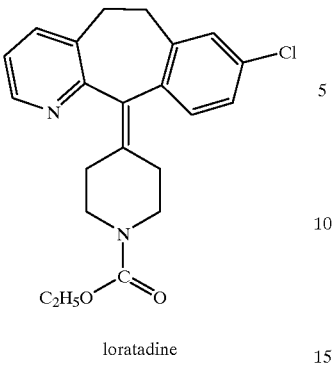

loratadine

Lithium diisopropylamide (LDA) solution was generated by adding 243 mL (0.389 mol) of 1.6M n-butyllithium solution in hexane to diisopropylamine (40.8 g, 0.404 mol) in xylene:THF (210:360 mL) at −20° to −5° C. After stirring in this range for 0.75 hours, the dimethyl phosphonate in xylene (100 g (0.377 mol) in 105 mL) was added in the range of −30 to −20° C. over 0.5 hours. The solution was stirred in this range for 1.5 hours and a solution of the 8-chloro-tricyclic-ketone in THF (85.0 g (0.349 mol) in 255 mL) was added over 0.75 hours in the range of −30 to −20° C. It was allowed to warm to −10° C. over 0.75 hours before being quenched with acetic acid (38 g, 0.633 mol). The yellow solution was heated to reflux, xylene (170 mL) was added and THF/hexane (about 910 mL) was distilled off to a solution temperature of 134° C. It was refluxed for 1.5 hours, cooled to 80° C., and water (340 mL) was added. It was refluxed for a further 1 hour and the phases separated (22% undecomposed hydroxyphosphonate intermediate was recovered from the aqueous phase by extraction with dichloromethane). The xylene phase was water washed and the solvent removed under reduced pressure. The residual material was recrystallised from acetonitrile to give 94.7 g (71% yield) of pure loratadine in 2 crops.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A process for preparing a compound having the formula:

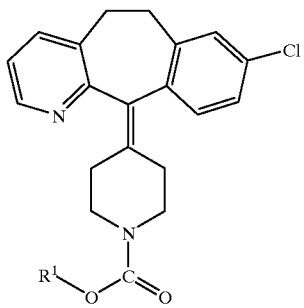

(I)

wherein $R^1$ is selected from the group consisting of: alkyl, alkenyl, alkynyl, aryl, aralkyl, cycloalkyl, and cycloalkylalkyl, $R^1$ being optionally substituted by substituents selected from halo, —OH, alkyl, alkoxy, or —CF$_3$, said process comprising the following steps:

(a) reacting a ketone having the formula

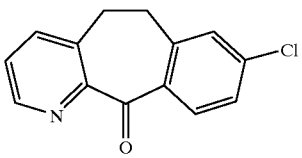

with a carbanion having the formula

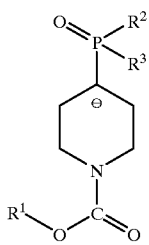

wherein $R^1$ is as defined above, and $R^2$ and $R^3$ are independently selected from the group consisting of —OR$^A$ and —R$^A$, wherein $R^A$ is alkyl, phenyl, substituted phenyl, cycloalkyl, substituted cycloalkyl, cycloalkylalkyl, or substituted cycloalkylalkyl;

(b) treating the reaction mixture from step (a) with a protonating agent; and (c) thermally decomposing the protonated product from step (b) to form the compound of formula (I).

2. The process of claim 1, wherein $R^1$ is alkyl.

3. The process of claim 1, wherein $R^1$ is ethyl.

4. The process of claim 3, wherein $R^A$ is alkyl.

5. The process of claim 4, wherein both $R^2$ and $R^3$ are —OR$^A$.

6. The process of claim 5, wherein both $R^2$ and $R^3$ are —OC$_2$H$_5$.

7. The process of claim 6, wherein the carbanion is formed by reacting a compound having the formula

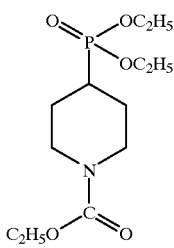

with an organolithium base.

8. The process of claim 7, wherein the organolithium base is lithium diisopropylamide.

9. A process for preparing a compound having the formula:

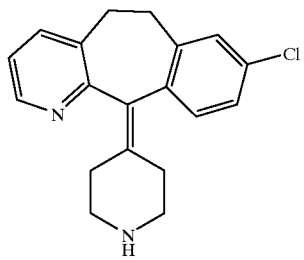

(IV)

said process comprising the following steps:
(a) reacting a ketone having the formula:

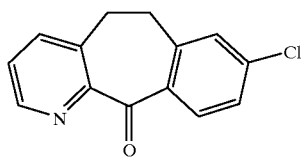

with a carbanion having the formula:

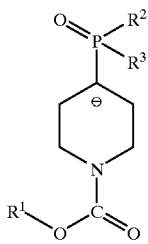

wherein $R^1$ is selected from the group consisting of: alkyl, alkenyl, alkynyl, aryl, aralkyl, cycloalkyl, and cycloalkylalkyl, $R^1$ being optionally substituted by substituents selected from halo, —OH, alkyl, alkoxy, or —$CF_3$; and $R^2$ and $R^3$ are independently selected from the group consisting of —$OR^A$ and —$R^A$, wherein $R^A$ is alkyl, phenyl, substituted phenyl, cycloalkyl, substituted cycloalkyl, cycloalkylalkyl, or substituted cycloalkylalkyl;

(b) treating the reaction mixture from step (a) with a protonating agent;

(c) thermally decomposing the protonated product from step (b) to form a compound having the formula

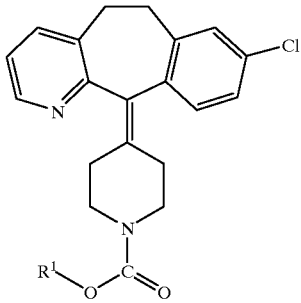

(I)

wherein $R^1$ is as defined above; and (d) converting the compound of formula (I) to the compound of formula (IV).

10. The process of claim 9, wherein $R^1$ is alkyl.

11. The process of claim 10, wherein $R^1$ is t-butyl.

12. The process of claim 11, wherein $R^A$ is alkyl, and step (d) is carried out by treating the compound of formula (I) with acid.

13. The process of claim 12, wherein $R^2$ and $R^3$ are both —$OC_2H_5$.

14. A compound having the formula:

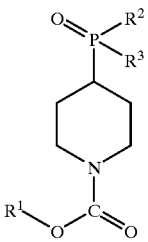

(III)

wherein $R^1$ is selected from the group consisting of: alkyl, alkenyl, alkynyl, aryl, aralkyl, cycloalkyl, and cycloalkylalkyl, $R^1$ being optionally substituted by substituents selected from halo, —OH, alkyl, alkoxy, or —$CF_3$; and $R^2$ and $R^3$ are independently selected from the group consisting of —$OR^A$ and —$R^A$, wherein $R^A$ is alkyl, phenyl, substituted phenyl, cycloalkyl, substituted cycloalkyl, cycloalkylalkyl, or substituted cycloalkylalkyl.

15. The compound of claim 14, wherein $R^1$ is alkyl and $R^A$ is alkyl.

16. The compound of claim 15, wherein $R^1$ is ethyl and both $R^2$ and $R^3$ are —$OC_2H_5$.

* * * * *